United States Patent [19]
Wilson

[11] Patent Number: 4,914,120
[45] Date of Patent: Apr. 3, 1990

[54] FUNGICIDAL IMADAZOLE KETONE DERIVATIVES

[75] Inventor: John R. H. Wilson, Kent, England

[73] Assignee: Shell Internationale Research Maatschappij, B.V., The Hague, Netherlands

[21] Appl. No.: 267,165

[22] Filed: Nov. 4, 1988

[30] Foreign Application Priority Data

Nov. 6, 1987 [GB] United Kingdom ............... 8726110

[51] Int. Cl.$^4$ .................... A01N 43/50; C07D 233/64
[52] U.S. Cl. ..................................... 514/400; 548/342
[58] Field of Search ......................... 548/342; 514/400

[56] References Cited

U.S. PATENT DOCUMENTS 4,684,659 8/1987 Karjalainen et al. ........... 514/400 X

OTHER PUBLICATIONS

Chemical Abstracts, 89:146843m, (1978), [N. Gor-bulenko et al., *Dopov. Akad. Nauk Ukr. RSR, Ser. B: Geol., Khim. Biol. Nauki* 1978, (7), 621-5].

*Primary Examiner*—Richard A. Schwartz

[57] ABSTRACT

The invention provides imidazole ketone derivatives of the general formula I:

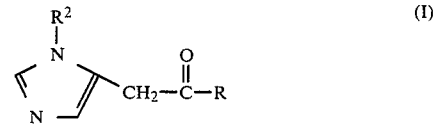

or an acid-addition salt or metal salt complex thereof, in which R represents a phenyl group substituted by one or more halogen atoms and $R^2$ represents an optically substituted alkyl group; processes for their preparation; compositions containing such compounds and their use as fungicides.

12 Claims, No Drawings

FUNGICIDAL IMADAZOLE KETONE DERIVATIVES

This invention relates to certain imidazole ketone derivatives, a process for their preparation, compositions containing such compounds and their use as fungicides.

According to the present invention there is provided a compound of the general formula

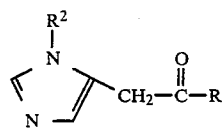  (I)

or an acid-addition salt or metal salt complex thereof, in which R represents a phenyl group substituted by one or more halogen atoms and $R^2$ represents an optionally substituted alkyl group.

When the compounds of this invention contain an alkyl substituent group, this may be linear or branched any may contain up to 12, preferably up to 6, and especially up to 4, carbon atoms.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include, for example, halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms.

It is preferred that R is a phenyl group substituted by 1 to 3 halogen, especially bromine, atoms.

Preferably, $R^2$ represents a $C_{1-12}$ alkyl, particularly a $C_{1-6}$ alkyl, group.

A particularly preferred sub-group of compounds of formula I is that in which R represents a bromophenyl group and $R^2$ represents a methyl group.

The present invention also provides a process for the preparation of a compound of formula I as defined above or an acid-addition salt or metal salt complex thereof which comprises reacting a compound of the general formula

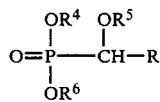  (II)

in which R is as defined above and $R^4$, $R^5$ and $R^6$, which may be the same or different, represent an alkyl, cycloalkyl, phenyl or benzyl group, with a compound of the general formula

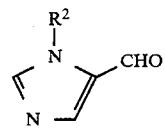  (III)

in which $R^2$ is as defined above, in the presence of a base, and, if desired, reacting the compound of formula I so obtained with a suitable acid or metal salt to form an acid-addition salt or metal salt complex thereof. A particularly preferred compound of formula II is that in which $R^4$, $R^5$ and $R^6$ all represent an ethyl group.

Suitable bases which may be used in the above process include sodium hydroxide, potassium hydroxide, potassium tert-butoxide, sodium hydride, and, most preferably, butyl lithium.

The process of the invention is conveniently carried out in the presence of a solvent. Suitable solvents include dimethylformamide, dimethyl sulphoxide, ethers, particularly tetrahydrofuran, and alcohols, such as ethanol. The reaction is suitably carried out at a temperature of $-100°$ C. to $100°$ C., the preferred reaction temperature being $-80°$ C. to $70°$ C.

The compound of formula II may be prepared according to the method described by D. Burkhouse and H. Zimmer in Synthesis, 1984, 330. Compounds of formula III may be prepared by the method described by R. G. Jones and K. C. McLaughlin in J. Amer. Chem. Soc., 1949, 71, 2444.

The compounds of general formula I have been found to have fungicidal activity. Accordingly, the invention further provides a fungicidal composition which comprises a carrier and, as active ingredient, a compound of formula I or an acid-addition salt or metal salt complex thereof as defined above. A method of making such a composition is also provided which comprises bringing a compound of formula I as defined above, or an acid-addition salt or metal complex thereof, into association with at least one carrier. Such a composition may contain a single compound or a mixture of several compounds of the present invention.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, or example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts or polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a plant, or could include an adhesive component enabling them to be applied directly to the stem of a plant.

The invention still further provides the use as a fungicide of a compound of the general formula I as defined above or an acid-addition salt or metal salt complex thereof or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include grain crops, particularly wheat and barley. The duration of protection is normally dependent on the individual compound selected, and also a variety of external factors, such as climate, whose impact is normally mitigated by the use of a suitable formulation.

The compounds of the present invention are also useful as intemediates in the preparation of other fungicidally active imidazole derivatives, such as the imidazole oxime derivatives which form the subject of our co-pending application (T532).

The invention is further illustrated by the following Examples.

EXAMPLE 1

Preparation of 4-bromophenyl 1-methyl-51-imidazolylmethyl ketone (R=4-bromophenyl; $R^2$=methyl)

Butyl lithium (2.4M, 11 ml) in hexane was added over a period of 5 minutes to a solution of diethyl 4-bromophenyl-ethoxymethylphosphonate (10.11 g, 30 mmol) in tetrahydrofuran (150 ml) at 78° C. under an atmosphere of nitrogen. After 10 minutes stirring, a solution of N-methyl 5-imidazolecarboxaldehyde (2.2 g)

in tetrahydrofuran (80 ml) was added and the reaction mixture was allowed to warm slowly to room temperature. Water (200 ml) and concentrated hydrochloric acid (25 ml) were added and the reaction mixture was refluxed for 4 hours and then cooled to room temperature. The reaction mixture was then neutralised with anhydrous sodium carbonate and the tetrahydrofuran evaporated. The residue was extracted with ethyl acetate (3×300 ml) and the combined organic extract was then washed with saturated sodium chloride solution, dried and concentrated by evaporating off the solvent. Flash chromatography of the residue on silica gel using 9:1 chloroform:methanol as eluant gave 4-bromophenyl 1-methyl-5-imidazolylmethyl ketone (4.9 g) as a white solid, m.pt. 109° C.

Analysis—Calc: C: 51.6; H: 3.9; N: 10.0%; Found: C: 51.2; H: 4.7; N: 11.1%.

EXAMPLE 2

The fungicidal activity of compounds of the invention was investigated by means of the following test.

Activity against barley powdery mildew (*Erysiphe graminis* f.sp. *hordei*; Eg)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with a solution of the test compound in 1:1 water/acetone containing 0.04% "TWEEN 20" (Trade Mark: a polyoxyethylene sorbitan ester surfactant) at a dosage of 1 kilogram of active material per hectare using a moving track sprayer. After drying, plants are returned to a compartment at 20°-25° C. and moderate humidity for up to 7 days, followed by assessment. Assessment is based on the percentage of leaf area covered by sporulation compared with that on leaves of control plants.

The extent of disease control in the above test is expressed as a rating compared with either an untreated control or a diluent-sprayed-control, according to the criteria:

0=less than 50% disease control
1=about 50–80% disease control
2=greater than 80% disease control The result of this test is set out in Table II below:

TABLE II

| Compound Example No. | Fungicidal Activity Eg |
|---|---|
| 1 | 2 |

I claim:
1. A compound of the formula:

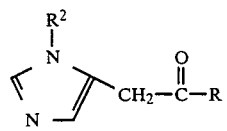
(I)

or an acid-addition salt or metal salt complex thereof, in which R represents a phenyl group substituted by one or more halogen atoms and $R^2$ represents an optionally substituted alkyl group.

2. A compound according to claim 1, in which $R^2$ represents a $C_{1-12}$ alkyl group optionally substituted by one or more substituents selected from halogen atoms, nitro, cyano, hydroxyl, $C_{1-12}$ alkyl, $C_{1-12}$ haloalkyl, $C_{1-12}$ alkoxy, $C_{1-12}$ haloalkoxy, amino, $C_{1-12}$ alkylamino, di-$C_{1-12}$ alkylamino, formyl, $C_{1-12}$ alkoxycarbonyl, carboxyl, $C_{1-12}$ alkanoyl, $C_{1-12}$ alkylthio, $C_{1-12}$ alkylsulphinyl, $C_{1-12}$ alkylsulphonyl, carbamoyl, and $C_{1-12}$ alkylamido groups.

3. A compound according to claim 1, in which R represents a phenyl group substituted by 1 to 3 halogen atoms.

4. A compound according to claim 3, in which the halogen atoms are bromine atoms.

5. A compound according to claims 1, 2, 3 or 4 in which $R^2$ represents a $C_{1-6}$ alkyl group.

6. A compound according to claim 1, in which R represents a bromophenyl group and $R^2$ represents a methyl group.

7. A fungicidal composition comprising a carrier and, as an active ingredient, a fungicidally-effective amount of a compound of the formula:

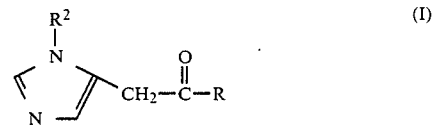
(I)

or an acid-addition salt or metal salt complex thereof, in which R represents a phenyl group substituted by one or more halogen atoms and $R^2$ represented an optionally substituted alkyl group.

8. A composition according to claim 7, which comprises at least two carriers, at least one of which is a surface-active agent.

9. A method of combating fungus at a locus, which method comprises treating the locus with a fungicidally-effective amount of a compound of the formula:

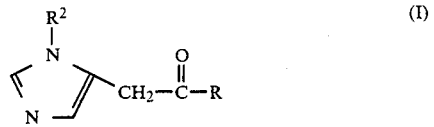
(I)

or an acid-addition salt or metal salt complex thereof, in which R represents a phenyl group substituted by one or more halogen atoms and $R^2$ represents an optionally substituted alkyl group.

10. A method of combating fungus at a locus, which method comprises treating the locus with a fungicidal composition according to claim 7.

11. A method according to claim 10, wherein said composition comprises at least two carriers, at least one of which is a surface-active agent.

12. a method according to claim 9, wherein said locus comprises plants subject to or subjected to fungal attack, seeds of such plants or the medium in which the plants grow or are to be grown.

* * * * *